United States Patent [19]

Kaneda et al.

[11] 3,993,756

[45] Nov. 23, 1976

[54] ANTILIPEMIC AGENT CONTAINING A SOYBEAN OIL FRACTION

[76] Inventors: Takashi Kaneda, No. 14-1-44, Sanjo, Sendai, Miyagi, Japan; Toshikazu Tabata, No. 748, Kikuna, Kohoku, Yokohama, Japan

[22] Filed: Feb. 11, 1975

[21] Appl. No.: 549,047

Related U.S. Application Data

[63] Continuation-in-part of Ser. No. 358,537, May 9, 1973, abandoned.

[52] U.S. Cl. .............................................. 424/195
[51] Int. Cl.² ........................................ A61K 35/78
[58] Field of Search .................................... 424/195

[56] References Cited
OTHER PUBLICATIONS

Bartov et al., Chem. Abst., vol. 74, (1971), p. 73626w.

Kaneda et al., Chem. Abst., vol. 67, (1967), p. 19107v.

*Primary Examiner*—Sam Rosen
*Attorney, Agent, or Firm*—Lane, Aitken, Dunner & Ziems

[57] ABSTRACT

Therapeutic compositions containing a nonsaponifiable fraction of soybean oil are disclosed. The nonsaponifiable fraction of soybean oil may be combined with an orally administrable pharmaceutical carrier to treat lipemia.

7 Claims, 7 Drawing Figures

ANTILIPEMIC AGENT CONTAINING A SOYBEAN OIL FRACTION

CROSS-REFERENCE TO RELATED APPLICATION

The present application is a continuation-in-part of our copending application Ser. No. 358,537, filed May 9, 1973, now abandoned and entitled ANTILIPEMIC AGENT CONTAINING A SOYBEAN OIL FRACTION.

BACKGROUND OF THE INVENTION

This invention relates to an antilipemic agent containing a therapeutically effective amount of a nonsaponifiable fraction of soybean oil. Antilipemic agents are substances which act to lower the level of fats or lipids in blood serum. It also relates to an orally administrable therapeutic composition in the form of a pharmaceutical carrier and a nonsaponifiable fraction of soybean oil and to a method for treating lipemia using same.

It has been established in the prior art that certain plant sterols (also termed phytosterols), including β-sitosterol and stigmasterol, are effective for lowering the cholesterol level in blood serum[1]. A number of such reports on the antilipemic activity of plant sterols have been published. An antilipemic agent containing 20% by weight of β-sitosterol suspended in a 4% alcohol solution has recently been put on the market by E. Lilly Co. At the present time there exists no known method by which plant sterols other than β-sitosterol, e.g., stigmasterol and campesterol, can be extracted and separated, in pure form, from vegetable oils. The use of β-sitosterol as an antilipemic agent requires that dosages be administered in disadvantageously large amounts, i.e., 20 to 30 g of β-sitosterol per day, because of the body's low absorption of β-sitosterol[1], thus inviting liver or kidney troubles over long periods of administration. Additionally, where the β-sitosterol containing antilipemic agent is administered over a long period of time, a rebound phenomenon in the cholesterol value is observed during the administration period.

[1]See, for example, *Steroid Biochemistry and Pharmacology* M. H. Briggs and J. Brotherton — Academic Press (London:1970), p. 183.

SUMMARY OF THE INVENTION

It has now been discovered that when an antilipemic agent composed mainly of a nonsaponifiable fraction of soybean oil is used, the dosing amount can be reduced to less than 1/10th (1.2 – 1.8 g per day) that required for β-sitosterol, thus avoiding potential kidney and liver problems. Blood and urine examinations show that the newly discovered antilipemic agent produces no adverse secondary effects even when administered over a long period of time. Furthermore, it has been confirmed through laboratory and clinical studies that the plant sterols become substituted for a part of the animal sterols (cholesterols) in the liver and blood. The agent containing the nonsaponifiable matter of soybean oil should be administered in doses containing no more than 600 to 900 mg of phytosterols to attain a satisfactory clinical result. It has been discovered that where the nonsaponifiable fraction of soybean oil is administered to human beings in total dosages of 1200 to 1800 mg a day, the total cholesterol level in the blood serum is lowered on the average of 10 to 15%, but the true lowering of the cholesterol level is thought to be about 20 to 25% since about 10% of the cholesterols in the serum are replaced by phytosterols.

From the foregoing, it will be understood that the antilipemic agent of the present invention offers the advantage that the dosage can be significantly reduced as compared with the prior art β-sitosterol-containing agent which required total dosages of 20 to 30 g per day.

Accordingly, it is an object of the present invention to provide an antilipemic agent which is effective for reducing serum lipids without causing undesirable secondary effects.

DESCRIPTION OF THE PREFERRED EMBODIMENTS

Figure 1:
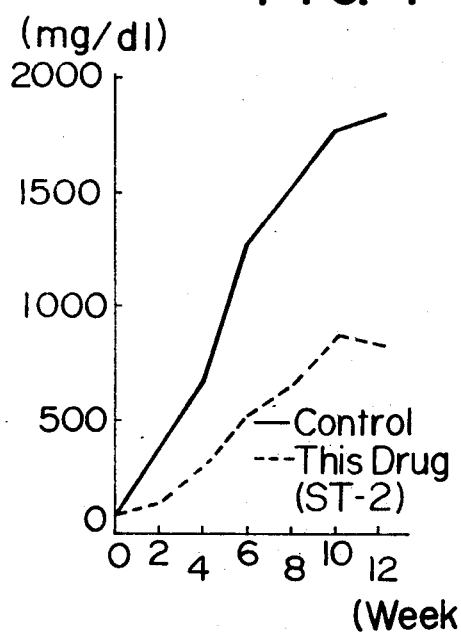
FIG. 1 is a graph showing changes in the total amount of cholesterol in the serum of two groups of rabbits occuring during a 12 week period in which the rabbits were fed in the manner of example No. 7.

The unsaponifiable fraction of soybean oil which is employed as an active component of the antilipemic agent of the present invention can be prepared by saponifying and subjecting to molecular distillation a deodorized soybean oil. The oil fraction so produced contains large amounts of phytosterols and tocopherols. Analysis of the unsaponifiable fraction of soybean oil by a color reaction test, a digitonide-formation reaction test, infrared and ultraviolet absorption spectra, and thin layer and gas liquid chromatography, reveals that the following substances are contained in the unsaponifiable fraction: plant sterols: β-sitosterol, stigmasterol and campesterol; natural tocopherols: α-, γ- and δ-tocopherols; fatty acids: lauric, myristic, palmitic and linoleic acids; and a small amount of squalane.

Various theories have been advanced to explain the physiological activity of α-tocopherol (vitamin E) which is a constituent of the unsaponifiable fraction of soybean oil, one of which is a biological antioxidant theory. It has been theorized that α-tocopherol has antioxidant properties because of the fact that animals deficient in vitamin E have in their body compounds which are considered to be peroxides of lipids. According to another theory, vitamin E directly takes part in an enzyme reaction, reducing cytochrome C in the presence of unsaturated fatty acids. Other interesting theories concerning vitamin E have been advanced, including a theory in which vitamin E is involved in the biosynthesis of and retention within body of ubiquinone. Another theory is that a lack of vitamin E gives rise to peroxidation of unsaturated aliphatic acids which are contained in living membranes, thus changing the transmittance or diffusing characteristics of the membranes.

As indicated above, the tocopherols are considered to have many unexpected physiological effects other than that of an antioxidant and may accordingly prove useful in a variety of applications as medicines. The medicinal action of the nonsaponifiable fraction of soybean oil used in the present invention appears to be due to the tocopherols which are present in large amounts in the nonsaponifiable fraction.

The unsaponifiable fraction of soybean oil of the present invention is a product which is obtained by the distillation and condensation of natural soybean oil. It is not now possible to artificially prepare an agent having the same composition as the distillate.

At the present time, it is also difficult to scientifically explain the reasons for the physiological potentiation of the components contained in the oil fraction or for the reduction of the undesirable side effects.

Experiments indicate that a nonsaponifiable fraction of soybean oil having a composition of about 40–50% by weight plant sterols and about 18–22% by weight tocopherols is preferred for use as an antilipemic agent. Most preferred is a nonsaponifiable fraction of soybean oil prepared in a manner as to have about 45% by weight plant sterols and about 20% by weight tocopherols. The content of plant sterols and tocopherols depends upon the type of soybean oil used. The nonsaponifiable fraction of soybean oil of the present invention, can be prepared using crude fatty acids of soybean oil (deodorized soybean oil distillate) containing about 25% by weight of plant sterols and about 18% by weight of tocopherols by subjecting the same to esterification with methanol and then to molecular distillation to separate free fatty acids therefrom, then recovering the nonsaponifiable fraction which contains about 45% by weight of plant sterols and about 20% by weight of tocopherols.

The nonsaponifiable fraction of soybean oil used in the present invention is an opaque, brown semi-solid at room temperature and becomes a semi-transparent oily liquid when heated to a temperature higher than about 80° C. The nonsaponifiable fraction has a distinctive odor and tastes slightly sweet.

The nonsaponifiable fraction of soybean oil shows selective solubility in various solvents. It is extremely soluble in chloroform, easily soluble in ether, sparingly soluble in acetone, hardly soluble in ethanol and almost insoluble in water. The solubility in these solvents for the nonsaponifiable fraction of soybean oil is as follows:

| Solvent | Solubility |
| --- | --- |
| Chloroform | 1 g/0.9 ml |
| Ether | 1 g/2.0 ml |
| Acetone | 1 g/500 ml |

-continued

| Solvent | Solubility |
| --- | --- |
| Ethanol | 1 g/5000 ml |
| Water | 1 g is insoluble in 10,000 l of water |

EXAMPLE 1 — TEMPERATURE STABILITY

Temperature, humidity and light stabilities of the nonsaponifiable fraction of soybean oil of the present invention have been determined. With regard to temperature stability, where an unsaponifiable fraction of soybean oil was placed in a transparent wide-mouthed medicine bottle and the bottle sealed with a metal stopcock and allowed to stand at room temperature over a two year period, the nonsaponifiable fraction changed color from brown to yellowish brown but showed no shift in the maximum and minimum ultraviolet absorption spectra, at 295 nm and 261 nm respectively in ethanol solution. Furthermore, the content of tocopherols was found to be reduced only by about 2% by weight after the first year and by about 10% after two years. Where an excipient such as $SiO_2$ was granulated and encapsulated, no changes in color or in tocopherol content were noted over a like period of time.

EXAMPLE 2 — HUMIDITY STABILITY

In order to test the humidity stability of the non-unsaponifiable fraction, the nonsaponifiable fraction was granulated and encapsulated and the resultant granules were placed in nine different containers, the atmosphere within each container being regulated using different saturated salt solutions. After exposure within the containers for 15 days, the hygroscopicity of the respective granules was measured.

The results of the humidity tests are given in Table 1 below.

Table 1

| | Control | Relative Humidity during Reservation (R.H.) % | | | | | | | | |
| --- | --- | --- | --- | --- | --- | --- | --- | --- | --- | --- |
| | | 20.4 | 40.2 | 53.7 | 70.2 | 79.1 | 82.3 | 85.6 | 90.3 | 95.5 |
| Hygroscopicity | Nil | Nil | Nil | Nil | Yes | Yes | Yes | Yes | Yes | Yes |
| Color | Pale Yellow | Pale Yellow | Pale Yellow | Pale Yellow | Yellow | Yellow | Yellow | Yellow | Dark Yellow | Dark Yellow |

The saturated salt solutions employed in the above measurements were as follows:

| Salt | Relative Humidity (%) |
| --- | --- |
| $CH_3COOK$ | 20.4 |
| $CrO_3$ | 40.2 |
| $NaBr-2H_2O$ | 53.7 |
| $NaNO_3$ | 70.2 |
| $(NH_4)_2SO_4$ | 79.1 |
| KCL | 82.3 |
| $K_2CrO_4$ | 85.6 |
| $KNO_3$ | 90.3 |
| $K_2SO_4$ | 95.5 |

The saturated salt solutions shown in the left-hand column above, maintain the respective Relative Humidities shown in the right-hand column when kept in sealed bottles at 37[C.

As is apparent from Table 1, the encapsulated nonsaponifiable fraction of soybean oil is stable below a relative humidity of about 60%. The data indicates that the critical humidity for stability of the nonsaponifiable fraction of soybean oil is 63.1%.

EXAMPLE 3 — LIGHT STABILITY

The light stability of the nonsaponifiable fraction was measured, with and without encapsulation, by irradiating samples by means of a low temperature xenon fade meter with a light quantity (about 180 Langley, ultraviolet ray having 300 – 400 nm) corresponding to that of 10 day's direct sunlight, averaged through a year. During the irradiation period, the samples were observed for changes in color and odor, and were subjected to qualitative analysis, to measurement for ultraviolet spectra absorption, to thin layer chromatography and to quantitative analysis. In the case of those samples of the nonsaponifiable fraction of soybean oil not encapsulated, the color changed from brown to yellowish brown, and the wavelengths of the maximum and minimum absorption spectra at 295 nm and 261 nm in ethanol solution, respectively, did not shift at all, though the ratio of the light absorption spectra increased by about 3.5% after 5 days' irradiation and by about 8.7% after 10 days' irradiation. The content of tocopherols was reduced in an amount of about 6% after 5 days' irradiation, and of about 10% after 10 days' irradiation. On the other hand, with the encapsulated samples, the degree of change was smaller as compared with that of the samples not encapsulated: the ratio of ultraviolet absorption spectra was increased by 3.6% after irradiation for 5 days and by 5% after irradiation for 10 days; and the tocopherol content was reduced by 2% after irradiation for 5 days and by 6% after irradiation for 10 days.

TOXICITY TESTS

It will be appreciated from the above test results that antilipemic agents containing therapeutically effective amounts of the unsaponifiable fraction of soybean oil should be kept in a dark storage place. Experiments show that when the nonsaponifiable fraction of soybean oil (both encapsulated and nonencapsulated) is placed in a sealed container and shielded from light, it retains its therapeutic effectiveness for longer than two years.

The toxicity of the nonsaponifiable fraction of soybean oil which is used in the present invention was examined by means of an acute toxity test, a subacute toxicity test and a chronic toxicity test, which tests were conducted in the manner described below.

EXAMPLE 4 — ACUTE TOXICITY TEST

A number of dd mice (female and male) having a weight of 12 to 18 g and Wistar rats (female and male) having a weight of 60 to 90 g, both being procured when 4 weeks old and bred in a laboratory for 1 week, were employed as the test animals. Five mice and five rats were taken as each group in the test. A sesame oil solution of the nonsaponifiable fraction of soybean oil was dosed by stomach tube to these animal groups in accordance with the following prescriptions and each animal group thus treated was kept in a breeding box maintained at a temperature of 22 ± 2 C with a relative humidity of 55±5%.

| Mouse: | 8.0 g/kg through mouth |
| | 4.0 g/kg through hypodermic injection |
| | 2.0 g/kg through abdominal injection |
| Rat: | 8.0 g/kg through mouth |
| | 2.0 g/kg through hypodermic injection |
| | 1.0 g/kg through abdominal injection |

72 hours after dosing, the life signs of the test animals were observed and for 10 days thereafter to determine the $LD_{50}$ value. The test results are as follows:

$LD_{50}$(median lethal dosage): 72 hours after dosing, all of the mice and rats were alive and even after the subsequent 10 days, none had died. Thus, it was impossible to calculate a $LD_{50}$ value.

Toxic symptoms: No differences between the test animals and normal animals were observed with regard to toxic symptoms or behavior.

EXAMPLE 5 — SUBACUTE TOXICITY TEST

A number of Wistar male rats (weight: 120 – 160 g) and female rats (weight: 105 – 135 g), purchased when four weeks old and bred in a laboratory for 1 week, were employed as test animals. Ten male and ten female rats were taken for each group in the test. The unsaponifiable fraction of soybean oil was mixed with a powdered foodstuff and the mixture was dosed to each of the groups in the different amounts shown below. The dosed rats were kept in breeding boxes maintained at a temperature of 22±2° C with a relative humidity of 55±5%. The breeding boxes were ventilated 10 times per hour.

| Daily Dosing Amounts: | 9000 mg/kg |
| | 4500 mg/kg |
| | 2250 mg/kg |

The above differing dosing amounts were determined on the basis of results of preliminary experiments wherein rats were dosed with the unsaponifiable fraction over 2 weeks. The antilipemic agent of the present invention was administered by mouth to each group of rats (males and females being kept separately) daily in the three different dosing amounts mentioned above, by mixing the agent with a powdered foodstuff produced by Nippon Clare K.K. The dosing test was continued for 1 month, periodically measuring the weight of each test animal. The amounts of feed and water taken by each test animal were also monitored and the animals were observed for toxic symptoms. At the end of the two week dosing period, the test animals were subjected to a urinalysis (for determining pH, Protein and sugar values), a blood test (for determining number of red blood corpuscles, number of white blood corpuscles, amount of hemoglobin, and white blood pattern), a patho-morphological study (for examination of main organs by dissection and measurement of weight), and a biochemical study of serum (for measurement of GOT, GPT, Al-P, Ch-E, LDH, T.Ch, F.Ch, $Na^+$, $K^+$, $Cl^-$, serum protein and blood sugar).

The test results are summarized as follows.

1. General symptoms were the same as those of the controls with no deaths or toxic symptoms.
2. No significant changes in weight, or in the amount of feed and water consumed was noted for any animal.
3. No significant differences between the test groups and the control group were discovered by the blood tests.

4. The biochemical study of the blood serum of each test animal revealed no differences that could be attributed to differences in the amounts of the nonsaponifiable fraction administered.

5. No adverse effects on the weight of the organs or in the patho-morphological study were noted.

EXAMPLE 6 — CHRONIC TOXITY TEST

A number of Donryu male rats (weight: 90 – 130 g), purchased when four weeks old and raised for a suitable period of time, were used as test animals. Ten rats were taken for each group. The antilipemic agent containing the nonsaponifiable fraction of soybean oil was mixed with a powdered foodstuff, and the mixture was fed to each of the test animals in the different amounts shown below. The rats thus fed were kept in breeding boxes maintained at a temperature of 22±2° C with a relative humidity of 55±5%.

| Daily Dosing Amount: | 9,000 mg/kg |
| --- | --- |
| | 6,000 mg/kg |
| | 3,000 mg/kg |

In one group (of ten rats), three rats were dosed for 13 weeks and seven rats for 27 weeks. During the test period, the weight and feed intake of each rat were monitored while observing for toxic symptoms. After completion of the respective test periods, the test rats were subjected to a urinalysis (pH, protein, sugar), a blood test (number of red blood corpuscles, number of white blood corpuscles, amount of hemoglobin, white blood pattern), a patho-morphological study (examination of main organs by dissection and measurement of weight) and a biochemical study of the serum (measurement of GOT, GPT, Al-P, Ch-E, LDH, T.Ch, F.Ch, $Na^+$, $K^+$, $Cl^-$, serum protein and blood sugar). The test results are summarized below.

1. General symptoms of the rats fed the antilipemic agent were the same as those of the controls, with no deaths or toxic symptoms.

2. No optical-microscopic changes in the artery systems, coronary arthery, renal artery, etc., were noted.

3. In the kidneys no marked differences were observed in fat deposition, in the amount of glycogen, in generation of stellate cells, or in the parenthemal cells as compared to the control group.

4. No changes in myelopoietic functions were noted.

5. The biochemical examination revealed no unusual changes.

6. No significant differences were observed with respect to weight, food and water consumption, the items of the blood test, or with respect to the weight of the organs examined.

It will be appreciated from the above-summarized test results that the antilipemic agent of the present invention is extremely nontoxic, so that it is possible to administer the agent over a long period of time without incurring adverse effects.

The medicinal effects of the antilipemic agent of the present invention have been determined by laboratory tests on both animals and clinical cases. Several of such tests are described below.

EXAMPLE 7 — PHARMACOLOGICAL EFFECTS

Testing Method: A number of male rabbits were employed as test animals. The rabbits were purchased at a weight of about 2.0 kg and raised for about 2 weeks, allowing them to become acclimated to their new environment before being employed as test animals. Thirteen rabbits were employed in the test and the rabbits were divided into a control group and a test group. A solid foodstuff (produced by Nippon Clare K.K.), containing 1% by weight of cholesterol, was fed each day to both groups of rabbits in the amount of 100 grams per rabbit. Water was supplied ad likitum by means of an automatic water-feeding apparatus. The antilipemic agent was administered to the test group in capsule form in the amount of 1.7 g per day for 12 weeks; the control group was fed potato starch in the same manner. The level of lipids in the blood serum of all the animals was measured in the manner described below using blood sampled from the ear vein, prior to the start of the test period and, thereafter, every two weeks during the test period.

| Total Cholesterols: | Kitamura's modified Zak-Henry method |
| --- | --- |
| Free Cholesterol: | Digitonin Method |
| Neutral Fats: | Van Handel-Kawade's improved Yamamoto Meth |
| Phospholipids: | Nakamura's modified Allen Method |
| Lipoprotein: | Electrophoresis Method |

A. Change in weight

The weights of the agent-dosed group rabbits as well as control group rabbits increased normally. In this respect, no differences were noted between the two groups.

B. Lipids in serum

1. Cholesterol

Figure 2:
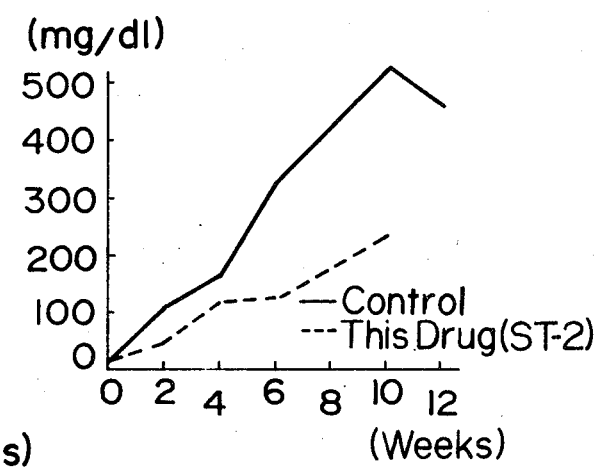
FIG. 2 is a graphical representation of changes in the total amount of free cholesterols in the serum versus time elapsed during the test of example No. 7.

A remarkable increase in the amount of total cholesterol and free cholesterol was noted in the control group, while the group to which the antilipemic agent was administered showed a relatively small increase in both total and free cholesterol which was about half that of the control group. FIG. 1 is a graphical representation of changes in the amount of total cholesterol in serum versus time elapsed during the test period for both the agent treated group and the control group. FIG. 2 is a graphical representation, similar to FIG. 1, of changes in the amount of free cholesterol in serum versus time. In these figures, "ST-2" designates the antilipemic agent of the present invention containing a nonsaponifiable fraction of soybean oil. The data shown in FIGS. 1 and 2 indicates that the antilipemic agent of the present invention effectively suppresses the increase of cholesterol in serum.

Figure 3:
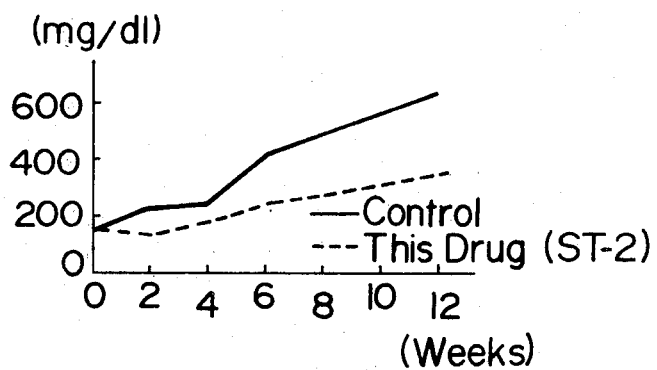
FIG. 3 is a graphical representation of changes in the amount of phospholipids in the serum versus time elapsed during the test period of example No. 7.

2. Phospholipids:

FIG. 3 is a graphical representation of changes in amount of phospholipids in the serum versus time elapsed, in the test period for both the agent treated group and the control group. As is apparent from FIG. 3, the antilipemic agent of the present invention is also effective in suppressing the increase of phospholipids in serum.

Figure 4:
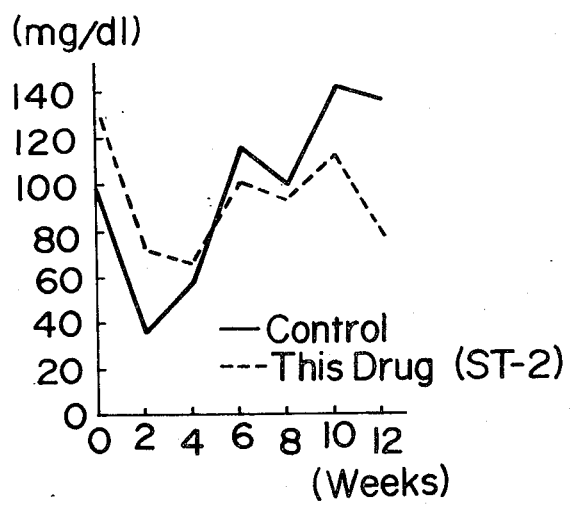
FIG. 4 is a graphical representation of changes in the amount of neutral fat in the serum versus time elapsed during the test period of example No. 7.

3. Neutral Fat:

FIG. 4 is a graphical representation of changes in the amount of neutral fat in the serum versus time elapsed, for both the agent-treated group and the control group. As shown in FIG. 4, the neutral fat value for the agent-treated group was slightly higher than that of the control group before commencement of the test, but became lower than that of the control group after 6 weeks of the dosing. After 12 weeks, the neutral fat value of the agent-dosed group was reduced to half that for the control group.

Figure 5:
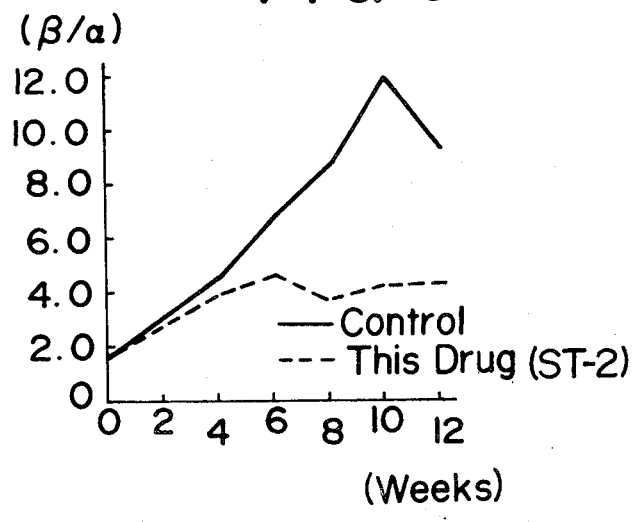
FIG. 5 is a graphical representation of changes in the amount of lipoproteins in the serum versus time elapsed during the test period of example No. 7.

4. Lipoprotein in Serum:

FIG. 5 is a graphical representation of changes in the amount of lipoproteins in the serum versus time elapsed for the agent-treated group and for the control group. As shown in FIG. 5, in the control group, the ratio of β-lipoprotein to α-lipoprotein sharply increased, while in the agent-dosed group, the ratio increased only slightly and reached a constant value after 8 weeks of the dosing. Thus, the data indicates that the antilipemic agent of the present invention also suppresses the increase of formation of lipoprotein in serum.

C. Lipid in viscera (liver cholesterol)

As shown in Table 2, below, the total amount of cholesterol in viscera and free cholesterol in viscera of the agent-treated group were reduced to low values, differing significantly from the control group.

Table 2

| Group | Liver Cholesterol Total (mg/g) | Free (mg/g) | Free % |
|---|---|---|---|
| Control | 4.57 (± 0.890) | 1.09 (± 0.166) | 24.84 (± 1.433) |
| ST-2* | 1.39** (± 0.343) | 0.47** (± 0.068) | 38.24** (± 2.694) |

Notes:
*-The antilipemic agent of the present invention
**-There exists a significant difference in p 0.01±S.E. (S.E. = standard error)

D. Plant sterols contained in serum and liver

The amount of total cholesterol contained in the serum and liver was measured by a colorimetric analysis in which a compound having a sterol ring induces a reaction. If plant sterols are present in a sample, a color reaction identical to that for cholesterol takes place. Therefore, where the amount of total cholesterol in the serum was determined after administration of the antilipemic agent of the present invention, this total cholesterol value is regarded as a sum of values for cholesterol and plant sterols. Accordingly, the use of a value for total cholesterol does not reflect a correct diagnosis for lipemia. Thus, in order to correctly determine the cholesterol level in each viscus and serum sample, it is necessary to correctly determine and subtract the amount of plant sterols. The plant sterol value can be determined using an FID gas liquid chromatography in combination with thin layer chromatography.

EXAMPLE 8A — TEST ON LABORATORY ANIMALS

Four groups of white rats were used in this test. One control group was fed with a cholesterol-free foodstuff while a second control group was fed a 0.5% cholesterol-containing foodstuff. A third group was fed with a cholesterol-added foodstuff, containing 1.5% by weight of plant sterols, and the fourth group was fed with a cholesterol-added foodstuff containing the antilipemic agent of the present invention. These foodstuffs were fed to the respective groups for four weeks. At the conclusion of the four week test period, the cholesterol values in the serum and as liver lipids were determined, and the lipid fractions of the serum and liver samples were analyzed by FID gas-liquid chromatography in combination with thin layer chromatography. The test results are shown in Table 3, below. It is apparent from Table 3 that about 50% by weight of the total cholesterol value represented substituted plant sterols. Accordingly, the value which is obtained by subtracting the plant sterol value from the total cholesterol value is considered to be a true cholesterol value for serum and as liver lipids. The data shows that when the antilipemic agent of the present invention is fed to rats, the true cholesterol value is reduced to a remarkable degree.

Table 3

Components and level of sterols in serum (plasma) and liver lipids of rats fed with soy-sterols (EXAMPLE 8A)

| | Group | (Plasma) Serum Sterol mg/dl | | | | Liver Sterol mg/g | | | |
|---|---|---|---|---|---|---|---|---|---|
| | | Total Cholesterol | Cholesterol | Stigmasterol | β-sitosterol | Total Cholesterol | Cholesterol | Stigmasterol | β-sitosterol |
| I | Food stuff without cholesterols | 160 | 160 | — | — | 2.8 | 2.8 | — | — |
| II | Food stuff containing 0.5 % by weight of cholesterols | 195 | 195 | — | — | 60.0 | 60.0 | — | — |
| III | Food stuff containing 1.5 % by weight of fractions mainly composed of plant sterols | 160 | 87 | 73 | | 6.4 | 4.6 | 1.3 | 0.5 |
| IV | Food stuff containing 1.5 % by weight of antilipemic agent of the invention | 147 | 81 | 50 | 16 | 5.6 | 1.7 | 2.8 | 1.1 |

EXAMPLE 8B — CLINICAL TESTS

The antilipemic agent of the present invention used in tests 8(A) and 8(B) and in the clinical test (example 9) described hereinafter, was administered orally in capsule form, each capsule containing 200 mg of the unsaponifiable fraction of soybean oil.

A. Test on Healthy Subjects

A predetermined amount of food (about 2700 Cal per day), including meats of high fat content (fat: 40%), was fed to each of nine healthy subjects for 6 weeks. During this test, a placebo was given to the subjects daily for the first one week, and during the next four weeks, the antilipemic agent was administered. During the last week, the placebo was again administered. In each case, 6 capsules were used daily for dosing. The values for total cholesterol and for plant sterols in the serum of the tested subjects were determined by Zak-Henry's method and by the method previously described in example 2A, respectively.

It was determined that plant sterols accounted for 10% by weight of the total cholesterol in the serum. Furthermore, one week after completion of the treatment with the antilipemic agent of the present invention, plant sterols could not be detected in the serum in any amount. The test results are shown in Table 4 below.

As is apparent from Table 5, the total serum lipid cholesterol value was reduced by 13.5% on average ($P<0.05$) by treatment with the antilipemic agent of the present invention, as compared to the placebo con- Table 4

Changes in biochemical components of serum lipids caused by Placebo and ST-2

| Items examined | Dosed agent | Value before dosing | Placebo Value after one week | ST****-2 Value after one week | Value after two weeks | Value after three weeks | Placebo Value after one week |
|---|---|---|---|---|---|---|---|
| GOT | ($\mu$) | 19 | 12 | 9 | 12 | 9.6 | 13.4 |
| GPT | ($\mu$) | 15 | 11 | 6 | 9 | 4.2 | 11.3 |
| ALP | ($\mu$) | 7.1 | 5.0 | 4.8 | 4.6 | 5.7 | 4.5 |
| LDH | ($\mu$) | 280 | 200 | 250 | 280 | 260 | 290 |
| TCH | (mg/dl) | 197±25 | 228±36 | 240±40 | 240±40 | 240±29 | 240±62 |
| PS* | (mg/dl) | 0 | 0 | 21 | 20 | 24 | 0 |
| $\beta$-Lip. pro. | (mg/dl) | 325±122 | 321±98 ○ | 300±82 | 230±94 | 246±106 ⊙ | 280±90 |
| T.T.** | ($\tau$/ml) | 6.1±4.7 | 7.5±1.0 | 4.8±3.0 | 9.2±3.1 | 15.3±4.3 | 17.1±4.6 |
| TBA *** | ( /ml) | 0.058 | 0.05 | 0.072 | 0.068 | 0.06 | 0.06 |

*PS:Phytosterol
**T.T.:Total tocopherol
***TBA:Thiobarituric acid value
****ST-2: This drug ○:$p<0.05$ ⊙:$p<0.01$ where p represents confidence limits.

B. Test on Patients

This test was conducted with 45 patients who were hypertensive and had total serum lipid cholesterol levels higher than 220 mg/dl. Nine capsules of a placebo were administered orally daily to each patient for the first three weeks of a six week test period, and nine capsules of the antilipemic agent of the present invention were orally administered daily for the next three weeks. The total cholesterol in the form of blood serum lipids was determined by ZakHenry's method, and the lipid fractions of the same serum were analyzed by a FID gas liquid chromatograph used in combination with thin layer chromatography. The results are shown in Table 5.

trol. Furthermore, if the substituted plant sterols, about 9% on average, are subtracted from the total cholesterol value, the true serum lipid cholesterol value becomes lower by 22.5% than the corresponding value for the placebo control. While the placebo was being administered, no plant sterols were detected in the serum.

5. Pathological Observation a. Visceral Observation

Heart: Fat deposition was noted in portions of the cardiac apexes and coronaries of both groups, but the number of cases showing such deposits was smaller for the antilipemic agent-treated group.

Spleen: A milk-white substance was found in both groups, but in a greater amount in the control group.

Table 5

| Case No. | Name | Sex | Age | Before dosing | After dosing of Placebo for three weeks mg/dl | After dosing of ST-2 for three weeks mg/dl | Amount reduced mg/dl | Sterols Plant sterols (%) P* | ST-2**** | Total Tocopherols mg/dl | GOT | Liver Functions GPT | ALP | LDH |
|---|---|---|---|---|---|---|---|---|---|---|---|---|---|---|
| 1 | T.T. | M* | 36 | 225 | 220 | 218 | -2 | 0 | 5 | 0.5 | 32 | 11 | 8.6 | |
| 2 | S.T. | M | 42 | 240 | 245 | 200 | -45 | 0 | 3 | 0.35 | 16 | 8 | 6.6 | 280 |
| 3 | K.K. | M | 50 | 232 | 270 | 240 | -30 | 0 | 20 | 1.35 | | | | |
| 4 | T.T. | M | 48 | 238 | 235 | 215 | -20 | 0 | 4 | 0.45 | | | | |
| 5 | M.M. | M | 59 | 293 | 285 | 230 | -55 | 0 | 10 | 0.70 | 15 | 8 | 5.8 | |
| 6 | T.T. | F*** | 56 | 307 | 310 | 300 | -10 | 0 | 25 | 0.45 | 74 | 29 | 12 | 560 |
| 7 | S.O. | F | 45 | 294 | 290 | 220 | -70 | 0 | 4 | 0.85 | 26 | 44 | 4 | 310 |
| 8 | N.T. | F | 40 | 271 | 275 | 240 | -35 | 0 | 8 | 1.90 | 13 | 7 | 3 | 200 |
| 9 | I.Y. | F | 52 | 255 | 265 | 250 | -15 | 0 | 21 | 1.70 | 26 | 29 | 4.7 | 130 |
| 10 | N.Y. | M | 74 | 290 | 280 | 230 | -50 | 0 | 18 | 1.70 | 13 | 8 | 4.9 | 210 |
| 11 | H.R. | F | 66 | 277 | 270 | 220 | -50 | 0 | 15 | 1.70 | 16 | 4 | | |
| 12 | K.T. | M | 62 | 198 | 205 | 200 | -5 | 0 | 10 | 1.20 | | | | |
| 13 | W.T. | M | 19 | 275 | 270 | 250 | -20 | 0 | 8 | 1.60 | 60 | 13 | 4.6 | 300 |
| 14 | K.T. | F | 78 | 285 | 290 | 240 | -50 | 0 | 6 | 1.50 | | | | |
| 15 | A.K. | M | 34 | 235 | 250 | 225 | -25 | 0 | 0 | 0.70 | 10 | 5 | 4.5 | 200 |
| 16 | I.K. | M | 58 | 275 | 260 | 210 | -50 | 0 | 7 | 0.90 | 64 | 58 | 6.7 | 240 |
| 17 | O.S. | M | 65 | 283 | 275 | 198 | -77 | 0 | 5 | 1.20 | 30 | 22 | 3.5 | 280 |
| 18 | S.K. | F | 45 | 260 | 275 | 230 | -45 | 0 | 3 | 1.30 | 25 | 22 | 9.9 | 240 |
| 19 | T.S. | M | 22 | 260 | 268 | 262 | -6 | 0 | 20 | 1.10 | 38 | 15 | 13.3 | 400 |
| 20 | M.S. | F | 43 | 235 | 255 | 231 | -24 | 0 | 22 | 0.80 | 30 | 18 | 5.3 | 430 |
| 21 | G.E. | F | 42 | 259 | 257 | 218 | -39 | 0 | 15 | 2.05 | | | 3.2 | 280 |
| 22 | H.S. | M | 53 | 290 | 288 | 255 | -33 | 0 | 28 | 1.55 | 126 | 112 | 13.3 | 280 |
| 23 | K.O. | M | 59 | 292 | 296 | 270 | -26 | 0 | 25 | 1.20 | 13 | 9 | 3.8 | 220 |
| 24 | M.K. | M | 72 | 302 | 312 | 260 | -52 | 0 | 22 | 0.90 | 27 | 20 | 0.7 | 430 |
| 25 | R.H. | M | 66 | 315 | 305 | 235 | -70 | 0 | 0 | 1.70 | 15 | 8 | 5.2 | 210 |
| 26 | S.K. | F | 69 | 205 | 208 | 208 | 0 | 0 | 4 | 0.60 | 18 | 11 | 4.3 | 200 |
| 27 | R.T. | F | 66 | 305 | 300 | 310 | +10 | 0 | 0 | 0.70 | 28 | 38 | 12.5 | 130 |
| 28 | K.K. | M | 73 | 289 | 297 | 227 | -50 | 0 | 22 | 0.75 | 60 | 15 | 11.0 | 490 |
| 29 | U.S. | F | 60 | 270 | 272 | 251 | -21 | 0 | 21 | 0.65 | 32 | 22 | 4.3 | 350 |
| 30 | T.M. | M | 67 | 260 | 268 | 240 | -28 | 0 | 8 | 1.10 | 36 | 16 | 5.6 | 320 |
| 31 | T.S. | M | 46 | 265 | 255 | 195 | -60 | 0 | 7 | 1.35 | 28 | 28 | 7.8 | 150 |

Table 5-continued

| Case No. | Name | Sex | Age | Before dosing | After dosing of Placebo for three weeks mg/dl | Sterols After dosing of ST-2 for three weeks mg/dl | Amount reduced mg/dl | Plant sterols (%) P* | Plant sterols (%) ST-2**** | Total Tocopherols mg/dl | GOT | Liver Functions GPT | Liver Functions ALP | Liver Functions LDH |
|---|---|---|---|---|---|---|---|---|---|---|---|---|---|---|
| 32 | A.A. | F | 63 | 269 | 265 | 196 | −69 | 0 | 0 | 0.95 | 70 | 19 | 11.0 | 400 |
| 33 | G.O. | M | 49 | 240 | 245 | 187 | −58 | 0 | 5 | 1.25 | | | | |
| 34 | T.I. | M | 66 | 276 | 280 | 220 | −60 | 0 | 0 | 1.60 | 66 | 28 | 12.2 | 270 |
| 35 | I.K. | M | 63 | 240 | 235 | 238 | +3 | 0 | 8 | 1.15 | 33 | 52 | 4.3 | 290 |
| 36 | I.I. | F | 58 | 207 | 215 | 200 | −15 | 0 | 7 | 0.80 | 10 | 15 | 3.8 | 200 |
| 37 | H.A. | F | 62 | 220 | 228 | 230 | +2 | 0 | 6 | 1.90 | 18 | 16 | 2.9 | 280 |
| 38 | S.T. | M | 60 | 223 | 219 | 200 | −19 | 0 | 2 | 1.70 | 35 | 15 | 5.3 | 240 |
| 39 | T.F. | M | 71 | 300 | 305 | 220 | −85 | 0 | 7 | 0.75 | 26 | 22 | 7.2 | 230 |
| 40 | S.S. | M | 61 | 305 | 309 | 300 | −9 | 0 | 8 | 0.95 | | | | |
| 41 | K.Y. | F | 55 | 325 | 320 | 295 | −25 | 0 | 0 | 1.35 | 57 | 48 | 3.6 | 450 |
| 42 | N.T. | F | 53 | 290 | 300 | 240 | −60 | 0 | 0 | 1.15 | 26 | 20 | 6.7 | 310 |
| 43 | M.K. | M | 69 | 229 | 225 | 190 | −35 | 0 | 0 | 1.55 | 14 | 6 | 3.1 | 290 |
| 44 | S.K. | F | 57 | 250 | 260 | 190 | −70 | 0 | 0 | 1.25 | 35 | 22 | 5.6 | 390 |
| 45 | M.M. | F | 61 | 266 | 270 | 195 | −75 | 0 | 0 | 0.80 | 38 | 13 | 6.7 | 300 |
| Average value ± Standard Deviation | | | | 265 ±30 | 267 ±30 | 231 ±31 | −36 | 0 | 9.1 ±8.5 | | | | | |
| P | | | | | P>0.05 | P<0.05 | Reduced ratio 13.5% | | | | | | | |

Total serum lipid cholesterols

NOTE
*:Placebo
**M:Male
***F:Female
****ST-2:This drug

Liver: Almost all of the control group were found to have a fatty liver, while most of the antilipemic agent treated group showed a normal liver color.

Aorta: In the control group, the degree of arteriosclerosis was greatest at the arch region with a downwardly weakening tendency toward the thorax and the abdominal region. Distinct fat deposits were also found in cardiac artery arteriomesenterial and renal artery openings. On the other hand, in the antilipemic agent-treated group, these symptoms were found in only 1 or 2 cases.

b. Weight changes of viscera

With regard to the kidney, lung and heart, no differences between the two groups was noted, but with regard to the liver, adrenal glands and spleen, the weights of these organs for the antilipemic agent-treated group was slightly smaller than that of the control group. A significant difference was noted only in liver weight.

c. Histological Examination

The aorta (arch region), heart, lumg, spleen, and adrenal glands were histologically examined.

Aorta: In the control group, generation or degeneration of foam[2/] cells took place. Furthermore, fat was diffusively deposited on portions of the median membrane in droplet or oval form. Additionally, a few instances of atheromatous degeneration within the aorta were noted which showed swelling and breakage of elastic fibers, and the proliferation or growth of glue-like fibers. In some cases within the control group, foam cells co-existed with a relatively large complex of

[2/] A foam cell is defined by Wesbster's as "A swollen vacuolated reticuloendothelial cell filled with lipide inclusions and characteristic of certian conditions involving disturbance of lipide metabolism". fat at the uppermost layer of the inner membrane and with fine droplets on the lower layer, indicating a slight degree of atheroma. In the other cases, there was either almost no change or a slight infiltration of lipids in the endothelia of the inner membrane.

Within the antilipemic agent-treated group, in only one severe case were granular fat deposits noted on endothelium of the aorta. Foam cells were also noted in the singular case. In the other cases within the treated group, no such conditions were noted.

Lung: Oedemalosous hypertrophy on the inner membrane of the artery walls was noted in two cases within the control group. No such symptoms were noted in any case within the treated group.

Heart: No fat deposits were noted on the myocardial fibers in any case, except for a slight accumulation of fat on the epicardium in a few cases within the control group. Membranic edemas on the aortic arch were noted in 4 cases within the control group, in which cases athermatous symptoms were distinctly visible. In one case within the agent-treated group an intimal edema was noted, slightly dyed with eosin.

Spleen: Nest-like fat deposits under the membrane were noted in four cases in the control group and in three cases in the agent-treated group, although the degree was different. In those three agent-treated cases, there was a slight hypertrophy of the spleen.

Liver: Although highly fatty liver symptoms were observed with the naked eye, there actually were only small deposits of fat globules in the liver cells and a pattern of circumferential pimelosis was observed. The fat deposits were noted mainly in the stroma or interstitial cells and in Kupffer's stellate cells, particularly in and around the center of the vein of the Glisson's capsule. These symptoms of the liver were, in a larger degree, found in the control group, and generally only slightly in the agent-treated group.

EXAMPLE 9 — CLINICAL TESTS

The following clinical tests were conducted at the Tokyo Medical College.

Test Method: 38 patients having diverse symptoms such as an ischemic heart-disease, hypertension, diabetes, acute hepatitis, and gastric ulcers were subjected to the clinical tests. The total cholesterol value in the serum was within the range of 205 to 335 mg/dl before treatment and had an average value of 260.4 mg/dl. 26 patients showed a total cholesterol level higher than 250 mg/dl, and 12 patients a value within a range of 205 to 248 mg/dl. Six capsules of the antilipemic agent of the present invention were fed orally to each of the patients daily for 4 to 20 weeks, or for 7.6 weeks on the average. 24 patients were administered an inactive placebo, instead of the agent, during the period between the 8th and 12th weeks, inclusive.

Results:

Serum Cholesterol Value:

The average value for serum cholesterols before treatment with the agent of the present invention was 260 mg/dl, which value was reduced to 225.9 mg/dl two weeks after commencement of the treatment and to 229.9 mg/dl four weeks after. The value rebounded to slightly higher levels, i.e., 232.2 mg/dl and 240 mg/dl respectively, 6 weeks and 8 weeks after the commencement of the treatment. In the 12th week after the placebo had been administered in place of the agent for 4 weeks, the value rose to 244.8 mg/dl.

β-lipoprotein:

i. Fried Hoeflmayr's Method

The average value for β-lipoprotein before treatment was 592.3 mg/dl, 2 weeks after commencement of the treatment it fell to 527.1 mg/dl, 4 weeks after 529.8 mg/dl, 6 weeks after 535.1 mg/dl and 8 weeks after 550 mg/dl. Thus, the value was reduced during the 2 to 6 week interval after commencement of the treatment. In the cases where the placebo was used after the eighth week, the values were 524.8 mg/dl 10 weeks later, and 520.7 mg/dl 12 weeks later. Thus, there appeared to be no rebound phenomenon.

ii. Capillary Precipitation Method

The average value for 11 test cases was 4.5 mm before commencing treatment with the agent of the present invention and was reduced to 3.7 mm 4 weeks after commencement, and to 4.0 mm 8 weeks after. Furthermore, in five cases, where the agent was administered for 4 weeks and then substituted with a placebo, the average value was 3.7 mm 8 weeks after. Therefore, no rebound phenomenon was evident.

GOT, GPT:

When GOT and GPT were studied in 38 cases, the average value of GOT before treatment was 31.2 and 25.1 after treatment, and those of GPT, before and after the treatment, were 32.9 and 26.2, respectively.

The Meulengracht's value and the ALP value were studied in 38 cases. The average of the Meulengracht's values was 6.9 before treatment with the agent and 6.8 after the treatment, and average values of ALP before and after the treatment were 8.8 and 8.6, respectively. These values remained relatively constant before and after the treatment, thus indicating that the agent of the present invention did not produce any ill effects.

Secondary Action:

No secondary effects were observed.

EXAMPLE 10 PREPARATION OF THE NONSAPONIFIABLE FRACTION OF SOYBEAN OIL:

The nonsaponifiable fraction of the present invention containing about 40–50% by weight plant sterols and about 18–22% by weight of tocopherols, can be prepared from deodorized soybean oil extract by the following procedure.

In order to obtain a natural medicine without decomposing the ingredients thereof, the sterol and tocopherol content in the deodorized soybean oil extract is controlled and the entire process is so conducted that a prescribed drug can be obtained through a single molecular distillation at a low temperature without resorting to a zinc dust cracking process as usually employed in isolating tocopherols.

The deodorized soybean extract starting material is obtained from the steam distillation operation which is the final step in the conventional soybean oil purification, or deodorizing process. The stem distillation is conducted at high temperatures and under reduced pressures. In the deodorizing system, the deodorized material is taken out at the trap of the steam distillation apparatus. Generally, the compositions of such extracts vary greatly depending on the deodorizing conditions such as temperature, degree of vacuum and quantity of steam.

Applying a Girdler's type dowtherm heating process and maintaining the deodorizing system at approx. 230° C and a reduced pressure in the range of 2 – 3 mmHg, steam was injected into the system at a rate of 5% per hour to produce (in the trap) a deodorized soybean extract containing sterols (25–30%), tocopherols (14–18%) and fatty acid (25–30%).

When 3000 g of methanol and 34 g of conc. sulfuric acid were mixed with 1740 g of the thus obtained deodorized extract and the resulting mixture was refluxed at 68° C for 3–4 hours, free fatty acid contained in the deodorized extract was converted into methyl ester. After stopping the reaction, the excessive methanol was removed under reduced pressure. The residual oily material (still residue), while maintained at 80°–100° C, was washed with 5 kg of warm water to remove the sulfuric acid.

After removing the water content completely by distillation, the methyl esters of fatty acids were removed at 170°–190° C and 20–130 μHg by molecular distillation. The resulting still residue was then purified to prepare the nonsaponifiable fraction of the present invention containing 40.0–50.0% sterols, and 18–22% tocopherols, the balance being about 30% higher fatty acids and trace amounts of other hydrocarbons. Table 6 gives actual compositions for products obtained in five different tests following the above procedure.

A. Part of plant sterols in the nonsaponifiable fraction of the invention apparently are present in the form of esters of higher fatty acids. Thus, these higher fatty acids produced by saponifying soysterol (material obtained by purifying the deodorized extract) were analyzed as follows.

TABLE 6

| | Deodorized soybean extract composition (%) | | Molecular distillation conditions | | | Result of distillation | | Purified material (soysterol) composition (%) | |
|---|---|---|---|---|---|---|---|---|---|
| | Sterol | Tocopherol | Distillation temperature | Pressure ($\mu$Hg) | Flow quantity (kg/hr) | Distillate (%) | Still residue (%) | Sterol | Tocopherol |
| 1 | 25 | 18 | 170° | 20 | 30 | 30 | 70 | 42 | 20 |
| 2 | 25 | 18 | 180° | 130 | 30 | 34 | 65 | 42 | 21 |
| 3 | 25 | 18 | 190° | 50 | 36 | 47 | 53 | 43 | 22 |
| 4 | 30 | 14 | 170° | 20 | 28 | 30 | 70 | 42 | 18 |
| 5 | 30 | 14 | 175° | 20 | 27 | 32 | 68 | 42 | 21 |

1. Identification of fatty acids by gas chromatography i. After saponifying 2 g of soysterol (material obtained by purifying the deodorized extract) in the method as previously described, sterols and oil contents were removed by extraction with ether and then the water layer was made acidic with dilute chloric acid and extracted three times, with about 20 ml of ether used for each extraction. Subsequently, all ether portions were collected together and washed with water, dehydrated with anhydrous sodium sultate and filtered. To the filtrate, after removing ether by distillation, was added 50 ml of acetone to prepare a mixture which was used for analysis of fatty acid.

Figure 6:
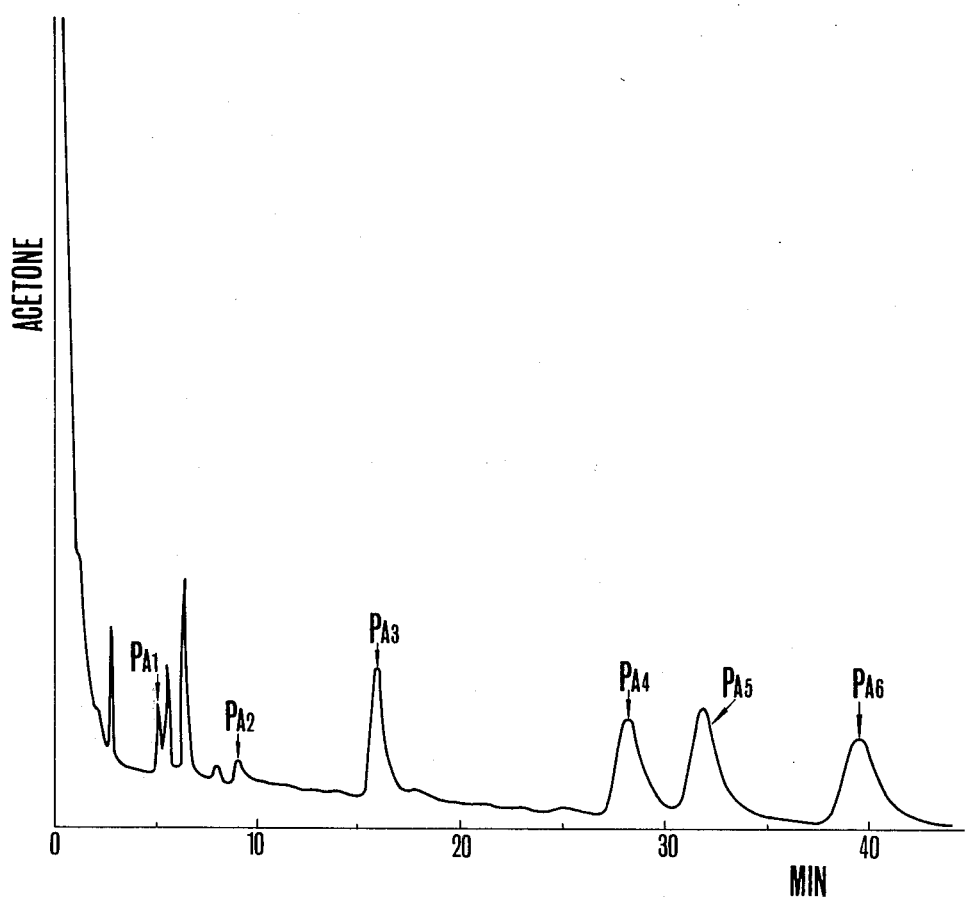
FIG. 6 is a graphical representation of a gas chromatogram of the fatty acid portion of the nonsaponifiable fraction of the present invention.
Figure 7:
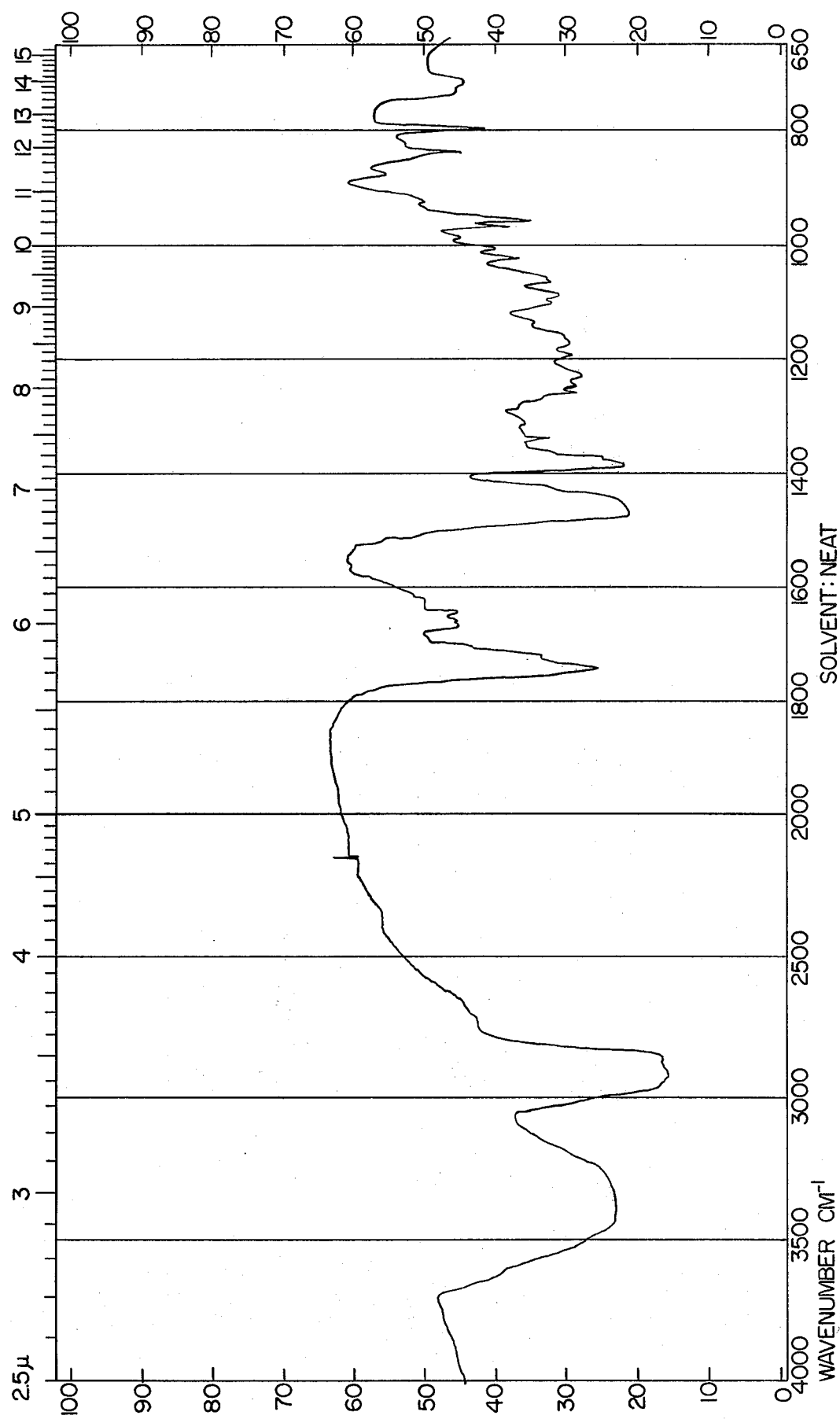
FIG. 7 is a graphical representation of the infrared spectrum of the nonsaponifiable fraction of the present invention.

The conditions for the gas chromatographic analyses were as shown in Table 8. As a column packing a mixture of DEGS (5%) and $H_3PO_4$ (1%) was used (herein expressed as DEGS-$H_3PO_4$ 5-1). The results of analysis were as shown in FIG. 6.

The fatty acids employed as the standard samples for identification were limited to those readily available in the market and presented distinguishing main peaks in the gas chromatogram, thus all the peaks of the fatty acid portion are not identified. The retention time and assignment of the peaks of the fatty acid portion were as shown in Table 7.

Table 7

| Peak No. (See FIG. 6) | Retention Time from Acetone | Assignment |
|---|---|---|
| $PA_1$ | 5.0 min. | Lauric acid |
| $PA_2$ | 8.9 min. | Myristic acid |
| $PA_3$ | 15.7 min. | Palmitic acid |
| $PA_4$ | 28.0 min. | Stearic acid |
| $PA_5$ | 31.4 min. | Oleic acid |
| $PA_6$ | 39.0 min. | Linoleic acid | ii. Saponification Value (S.V.)

S.V. is the number of mg of KOH required to neutralize a free acid or to saponify an ester contained in 1 g of fat.

Measurement 1 g of soysterol was accurately weighed out, to which was added accurately 25 ml of 0.5 N potassium hydroxide/ethanol solution. The mixture was then warmed for 1 hour using a reflux condenser with shaking from time to time in a water bath. When cooled the excess potassium hydroxide was neutralized with 0.5 N chloric acid using 1 ml of phenolphthalein reagent as an indicator.

TABLE 8

The conditions for the chromatogram shown in FIG. 6 were as follows:
Model: SHIMAZU-5A
Sample: Fatty acids portion of soysterol
% Acetone soln. 5$\mu$l
Column: St. Glass
  I. 3m I.D. 3mm

TABLE 8-continued

Packing: DEGS-$H_2PO_4$ 5–1%
Support: Chromosorb W
  mesh: 69–80
  treatment:
Carrier Gas: $N_2$
  flow rate: 65 ml/min.
$H_2$ flow rate: 50 ml/min.
Air flow rate: 650 ml/min.
Detector: FID. TCD.
  bridge   mA
  curr.
  appricd   V
V.
rad. source:
Range: 8 × 0.01 V
Sens.: $10^2$ MΩ
Temp.: col.: 208° C
  det.: 240° C
  inj.: 240° C
Chart speed: 5m-/min.

In a similar manner a blank was titrated with chloric acid.

The S.V. is calculated in accordance with the following formula:

$$S.V. = \frac{28.05 \times (b-a)}{\text{sample quantity}} (g)$$

where,
a: 0.5N chloric acid consumption (ml) with fatty acid sample added;
b: 0.5N chloric acid consumption (ml) in a blank test.

The actual measurement was 60. Thus, when calculated as linolic acid, the total fatty acid content in the soysterol is as follows:

$$\frac{S.V.}{N.V.} \times 100 = \frac{60}{198} \times 100 \approx 30\%$$

2. Fatty acid content in soysterol i. Method and principle of determination

Generally, the total fatty acid content in a fatty fraction is expressed by the following formula:

Percentage of total fatty acid in a fatty matter = $\frac{S.V.}{N.V.} \times 100$ where,
S.V.: Saponification Value
N.V.: Neutralization Value The foregoing formula was used for calculating the total fatty acid content in the soysterol.

ii. Neutralization Value (N.V.)

N.V. corresponds to the acid value of fatty acid and means the number of mg of KOH required for neutralizing 1 g of fatty acid. However, because of the fact that the fatty acid contained in the soysterol does not always have a constant composition, the N.V. value of linolic acid was used for convenience.

Measurement 0.5 g of linolic acid was accurately weighed and dissolved in neutral ethanol, which was then titrated with a 0.1N potassium hydroxide/ethanol solution, using phenolphthalein reagent as an indicator, until the solution presented a rose-pink color which remained for about 30 sec.

With the titration value expressed as Vml, then $$N.V. = \frac{5.6111 \times V(ml)}{\text{quantity of linolic acid}} (g)$$

the actual measurement was 198.

It was found that the nonsaponifiable fraction of this invention contained about 20% natural tocopherols, 40–50% plant sterols, about 30% higher fatty acids and a trace amount of other hydrocarbons.

The natural tocopherols appeared to consist of three different tocopherols: $\alpha$-, $\beta$- and $\gamma$-tocopherols.

The plant sterols appeared to consist of three different sterols: campesterol, stigmasterol and $\beta$-sitosterol.

The higher fatty acids include lauric acid, myristic acid, palmitic acid, stearic acid, oleic acid, linolic acid, etc.

It was also found that the trace hydrocarbons consisted mainly of a small quantity of squalene.

B. The method for analyzing the unsaponifiable fraction of the present invention and the results of such analyses are set forth below.

i. Determination of sterols and tocopherols:

The determination of sterols and tocopherols was effected in accordance with the method (refer to J. Am. Oil Chem. Soc., 45,848 (1968)) proposed by Nelson et al as described below.

Approximately 0.2 g of a sample was accurately ($\pm$ 0.0001 g) weighed into a 50 ml round bottom flask. Then, 4 ml of a 5% solution of pyrogallol in absolute ethyl alcohol was added to prevent oxidation of the tocopherols during saponification. A water cooled condenser was attached to the flask and the solution was heated to reflux, at which time 1 ml of 60% aqueous potassium hydroxide was added. The solution was allowed to reflux 3 min. and the flask was removed and cooled under tap water.

Distilled water, 20 ml, was added to the flask and the solution was transferred quantitatively to a 125 ml separatory funnel. Two 10 ml portions of diethyl ether were used to rinse the flask for quantitative transfer. The solution in the separatory funnel was extracted with the diethyl ether, taking care not to shake too vigorously to avoid forming an emulsion. The solution was extracted twice more with 25 ml portions of diethyl ether and the three diethyl ether extracts were combined. The combined extracts were transferred to a separatory funnel and washed with 20 ml portions of distilled water until washings were neutral to phenolphthalein indicator (usually 4 to 8 washings were required).

The diethyl ether solution was then transferred to a 100 ml round bottom flask and the diethyl ether was evaporated under nitrogen on a steam bath. When the diethyl ether was no longer visible, 4 ml of squalane solution were added with a pipet and the flask was swirled to insure complete solution of the residue. Approximately 2.5 $\mu$l of this solution were injected into the gas chromatograph. The results are shown in Table 9.

TABLE 9

| Conditions for measurement | |
|---|---|
| Column | 3 mm $\times$ 2 m St. |
| Column Packing | 1.5% SE-30 |
| Support | Chromosorb W |
| Carrier Gas | $N_2$ 150 ml/min. |
| $H_2$ | 50 ml/min. |
| Air | 350 ml/min. |
| Detector | FID |
| Range | 8 $\times$ 0.01 V |
| Sens. | $10^2$ M$\Omega$ |
| Temp. | |
| Column | 225° C |
| Detector | 270° C |
| Injection | 270° C |
| Relative Retention Times of Tocopherols and Sterols | |
| Squalene | 1.55 |
| $\delta$-Tocopherol | 2.06 |
| $\gamma$-Tocopherol | 2.72 |
| $\alpha$-Tocopherol | 3.40 |
| Campesterol | 3.89 |
| Stigmasterol | 4.25 |
| $\beta$-Sitosterol | 4.92 |

The calculation of tocopherol and sterol values was made by comparing the area of samples with that of standard samples.

ii. Determination of fatty acids:

For standards, 5 different fatty acid methyl esters were used in the form of acetone solutions prepared by dissolving varying quantities of methyl heptadecanoate as an internal standard matter and calibration curves were plotted.

To determine the intensity of peaks, the area measuring method was adopted. In practice, however, the peak intensity was measured by cutting the chromatogram chart paper along the peak lines and weighing the cut chart paper segments.

The following regression formulas were obtained from the calibration curves:

| Methyl palmitate | $y = 1.068x - 0.041$ |
|---|---|
| Methyl stearate | $y = 0.789x - 0.052$ |
| Methy oleate | $y = 0.353x + 0.026$ |
| Methyl linolate | $y = 0.795x + 0.026$ |
| Methy linoleate | $y = 0.611x - 0.054$ | y: peak area ratio
x: weight ratio

The samples were determined by use of the foregoing regression formulas.

4 g of each sample was accurately weighed out and introduced into a 100 ml brown measuring flask. Then the sample was dissolved in ether to accurately prepare a 100 ml sample solution.

0.5 ml of the thus prepared sample solution was poured into a spitz tube and standard solution, which has been prepared previously by dissolving 28.635 mg of an internal standard matter in 10 ml of acetone, was also introduced into the chromatograph in such a quantity (1–5 $\mu$l) as to develop peaks in the chromatogram having heights almost equal to those peaks developed by the sample. The results are shown in Table 10.

The conditions of gas chromatographic measurement were as follows:

| Column | 3 mm $\times$ 2 m stainless steel |
|---|---|
| Column Packing | DEGS* |
| Support | Shimalite |

| | | |
|---|---|---|
| Carrier Gas | N₂ | 40 ml/min. |
| H₂ Flow Rate | | 1.8 ml/min. |
| Air Flow Rate | | 0.8 ml/min. |
| Detector | FID | |
| Range | 8 × 0.01V | |
| Sens | 10² MΩ | |
| Column Tep. | 225° C | |
| Detector Tep. | 270° C | |
| Injection Tep. | 270° C | |

*diethylenen glycohol succinate

Preparation of granules containing the unsaponifiable fraction of soybean oil:

TABLE 10

| ANALYSES OF NONSAPONIFIABLE FRACTION | | |
|---|---|---|
| Sterols | Campesterol | 11.8% |
| | Stigmasterol | 11.7% |
| | β-Sitosterol | 20.2% |
| Tocopherols | δ-Tocopherol | 5.7% |
| | γ-Tocopherol | 2.9% |
| | α-Tocopherol | 11.9% |
| Fatty acids | Palmitic acid | 1.26% |
| | Stearic acid | 1.57% |
| | Oleic acid | 15.83% |
| | Linolic acid | 10.03% |
| | Linoleic acid | 1.25% |
| Others | | 5.86% |

The nonsaponifiable fraction prepared as illustrated above is generally used in an encapsulated granular form. In the granulation, it is necessary to use as an absorbent a compound which is highly oil-absorptive and which does not adversely affect the stability of the tocopherols contained in the nonsaponifiable fraction. The use of silicates as carriers should be avoided since such carriers may cause liver troubles.

The preferred granules are those which easily disintegrate, or fall to pieces in water, and which can be readily filled into hard capsules by means of automatic filling apparatus.

A highly purified silicic acid anhydride which is obtained by thermal hydrolysis of silicon tetrachloride (Trade Name: AEROSIL No. 200 – 400) was used as the absorbent to make the antilipemic agent administered in the tests described above.

The high purity silicic acid anhydride is first added to and mixed with the nonsaponifiable fraction of soybean oil, and the mixture is dried. The resultant product is then reduced to powdered form. An organic solvent such as chloroform, chlorothen, methylene chloride or the like, may be added to and kneaded with the powder which absorbs the solvent to produce granules having suitable properties for filling into capsules by the use of an automatic capsule-filling machine.

In the above-described preparation of the granules, it is preferable to use together with the organic solvent an organic slvent-soluble binding agent such as polyvinylpyrrolidone, a copolymer of 2-methyl-5-vinylpyridinemethacrylic acid, methylacrylate or the like, to improve the mechanical strength of the granules obtained and the quality of the tablets made therefrom. In order to further improve the solubility of the product in water, a small amount of a surface active agent such as sodium laurylsulfate, polyoxyethylene monostearate, polysorbate, or a derivative of castor oil or polyoxyethylene may be added to the mixture singly or in combination. Moreover, in order to stabilize the tocopherols in the nonsaponifiable fraction, a small amount of antioxidants and synergists of the antioxidants such as vitamin C, citric acid, etc. may be added.

The granules thus produced contain about 50% by weight of the nonsaponifiable fraction of soybean oil. They are suitably disintegrated by water, and they offer the further advantage that the stability of tocopherols contained therein is excellent, and they produce no kidney trouble.

EXAMPLE 11

470 g of the nonsaponifiable fraction of soybean oil, 20 g of vitamin C, 10 g of citric acid, 40 g of calcium cellulose glycolate, 20 g of sodium laurylsulfate, 10 g of polyoxyethylene monostearate and 600 ml of a halogenated hydrocarbon solvent were measured and sufficiently mixed to form a suspension. 390 g of AEROSIL No. 200 – 400 (Trade Name) were added and mixed with the suspension while agitating. The mixture was then dried at a temperature of about 50° to 60° C to give a solid material. The solid product was then pulverized to reduce to powdered form. To the powder was added 600 ml of a chlorothen-ethanol solution containing 40 g of polyvinylpyrrolidone. The resultant mixture was kneaded and then granulated using an ECK pelleter. The resultant granules were then dried at about 50° C to give a nontacky product. The content of the nonsaponifiable fraction of soybean oil in the granular product was 47% by weight. The granules readily disintegrated in water. Additionally, the stability of the tocopherols in the granular product was excellent.

A small amount of a lubricant such as magnesium stearate may optionally be added to the granular product to facilitate filling into capsules by means of conventional automatic capsule-filling machines.

We claim:

1. An antilipemic composition comprising a nonsaponifiable fraction of soybean oil in an amount effective to suppress the lipid content of blood serum, said nonsaponifiable fraction containing about 40–50% by weight plant sterols and about 18–22% by weight tocopherols, the balance being predominantly fatty acids, said nonsaponifiable fraction being obtainable by:
   steam distilling a crude soybean oil to recover a deodorized soybean oil extract in the trap of the distillation apparatus, said extract containing about 25–30% by weight plant sterols, about 14–18% by weight tocopherols and the balance being predominantly fatty acids;
   reacting methanol with said deodorized soybean oil extract to convert said fatty acids to the corresponding methyl esters, thus obtaining a mixture containing said methyl esters; and
   removing the fatty acid esters by molecular distillation at 170°–190° C and 20–130μ Hg to produce said nonsaponifiable fraction as the still residue.

2. The composition of claim 1 wherein said plant sterols constitute about 45% by weight of said nonsaponifiable fraction and said tocopherols constitute about 20% by weight of said nonsaponifiable fraction.

3. The composition of claim 1 wherein said plant sterols are selected from the group consisting of campesterol, stigmosterol, β-sitosterol and mixtures thereof.

4. The antilipemic composition of claim 1 additionally comprising an orally administrable pharmaceutical carrier.

5. The composition of claim 4 wherein said pharmaceutical carrier is a silicic acid anhydride.

6. The composition of claim 1 wherein said fatty acids constitute about 28–42% by weight of said nonsaponifiable fraction.

7. A method for treating the symptoms of lipemia in mammals which comprises administering to said mammals the composition of claim 1 to suppress the lipid content in blood serum of said mammals.

* * * * *

UNITED STATES PATENT OFFICE
CERTIFICATE OF CORRECTION

Patent No. 3,993,756     Dated November 23, 1976

Inventor(s) Kaneda et al

It is certified that error appears in the above-identified patent and that said Letters Patent are hereby corrected as shown below:

Column 1, line 39, after "a" insert --rebound phenomenon in the cholesterol value is observed during the administration period.--.

Column 1, lines 42 and 43, delete in their entirety.

Column 6, line 10 from bottom, change "T.Ch, F.Ch," to read --T·Ch, F·Ch,--.

Column 7, line 37, change "T.Ch, F.Ch," to read --T·Ch, F·Ch,--.

Column 8, line 9, "ad likitum" should read --ad likitum--

Column 13, line 53, change "lumg" to --lung--.

Column 13, line 66, after "of" insert --fat at the uppermost layer of the inner membrane and with fine droplets on the lower layer, indicating a slight degree of atheroma. In the other cases, there was either almost no change or a light infiltration of lipids in the endothelia of the inner membrane.--.

UNITED STATES PATENT OFFICE
CERTIFICATE OF CORRECTION

Patent No. 3,993,756   Dated November 23, 1976

Inventor(s) Kaneda et al

It is certified that error appears in the above-identified patent and that said Letters Patent are hereby corrected as shown below:

Column 13, lines 67 through 73 should read as a footnote as follows:

--2/A foam cell is defined by Webster's as "A swollen vacuolated reticuloendothelial cell filled with lipide inclusions and characteristic of certain conditions involving disturbance of lipide metabolism".--.

Column 16, line 23, change "stem" to --steam--.

Column 17, line 23, change "sultate" to --sulfate--.

Column 21, delete lines 11 and 12 in their entirety.

Column 21, insert the following heading before line 27 and after the end of Table 10:

--Preparation of granules containing the unsaponifiable fraction of soybean oil: --.

Column 21, line 53, change "slvent" to --solvent--.

Signed and Sealed this

Twenty-eighth Day of June 1977

[SEAL]

Attest:

RUTH C. MASON
Attesting Officer

C. MARSHALL DANN
Commissioner of Patents and Trademarks